(12) United States Patent
Fitzpatrick

(10) Patent No.: US 6,706,756 B1
(45) Date of Patent: Mar. 16, 2004

(54) VASODILATING COMPOUND AND METHOD OF USE

(75) Inventor: David F. Fitzpatrick, Brandon, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 10/065,770

(22) Filed: Nov. 18, 2002

Related U.S. Application Data
(60) Provisional application No. 60/332,428, filed on Nov. 16, 2001.

(51) Int. Cl.$^7$ ................................................ A61K 31/35
(52) U.S. Cl. ....................................... 514/456; 549/399
(58) Field of Search ........................... 514/456; 549/399

(56) References Cited

U.S. PATENT DOCUMENTS

| | | | |
|---|---|---|---|
| 4,925,871 | A | 5/1990 | Gabetta et al. |
| 5,594,032 | A | 1/1997 | Gonzalez-Cadavid et al. |
| 5,773,262 | A | 6/1998 | Ariga et al. |
| 5,891,459 | A | 4/1999 | Cooke et al. |
| 5,904,924 | A | 5/1999 | Garnor et al. |
| 5,912,363 | A | 6/1999 | Nafisi-Movaghar et al. |
| 5,945,452 | A | 8/1999 | Cooke et al. |
| 5,976,568 | A | 11/1999 | Riley |
| 6,007,824 | A | 12/1999 | Duckett et al. |
| 6,039,950 | A | 3/2000 | Khwaja et al. |
| 6,054,128 | A | 4/2000 | Wakat |
| 6,117,911 | A | 9/2000 | Grainger et al. |
| 6,149,939 | A | 11/2000 | Strumor et al. |
| 6,180,663 | B1 | 1/2001 | Lang |
| 6,200,558 | B1 | 3/2001 | Saavedra et al. |

OTHER PUBLICATIONS

Fitzpatrick, DF et al, 'Isolation and characterization of endothelium–dependent vasorelaxing compouds from grape seeds' J. Agr. and Food Chem. (2000), 48(12), 6384–6390.*
The Dominion Medical Briefing, West 2002 pp. 1 and 2.
ND Kim et. al., Ginsenosides Evoke Endothelium–Dependent Vascular Relaxation in Rat Aorta, Gen Pharmacol (FLK), Oct. 1994; 25 (6): 1071–7.
Emile Andriambeloson et. al., Nitric Oxide Production and Endothelium–Dependent Vasorelaxation Induced by Wine Polyphenols in Rat Aorta, British Journal of Pharmacology 1997.
Dr. John Briffa, Secret Healing Power in Your Christmas Tree, 2000 Associated Newspaper Ltd. Daily Mail (London).
Dr. John D. Folts, Ph.D., Synergistic Effect of Grape Seed and Grape Skin Extracts Points Toward Effectiveness of Whole Juice, According to Researcher, Food Ingredients Online News.
David F. Fitzpatrick et al., Isolation and Characterization of Endothelium–Dependent Vasorelaxing Compounds from Grape Seeds, vol. 48, No. 12, pp. 6384–6390.
D.F. Fitzpatrick et al., Grape Seed Procyanidins: Isolation, Identification, and Endothelium–Dependent Vasorelaxing Activity, The Journal of Heart Disease, 1(1):79 (May 1999).
David F. Fitzpatrick et al., Isolation, Identification, and Characterization of Grape Procyanidins Responsible for Endothelium–Dependent Vasorelaxing, Sub. to Welch's Jan. 21, 1999.
David F. Fitzpatrick et al., Endothelium–Dependent Vascular Effects of Pycnogenol, Journal of Cardiovascular Pharmacology, 32:509–515.
David F. Fitzpatrick et al., Endothelium–Dependent Vasorelaxing Activity of Wine and Other Grape Products, The American Physiological Society, 0363–6135/1993.
David F. Fitzpatrick et al., Endothelium–Dependent Vasorelaxation Caused by Various Plant Extracts, Journal of Cardiovascular Pharmacology, 26:90–95.
David F. Fitzpatrick et al., Endothelium–Dependent Vasorelaxing Activity of Wine, Grapes, and Other Plant Products, 1997 American Chemical Society.
David F. Fitzpatrick et al., Vasorelaxation, Endothelium, and Wine, 0951–6433/97, 1997 IOS Press.
Kathy's Herb Shop, Virilogarl by Olympian Labs—90 Capsul, http://www.kathysherbshop.com/shop.product75.html.
Whole Health MD.com, Supplements Grape Seed Extract, http://www.wholehealthmd.com/refshelf/substances_view/0,1525,793,00.html.
Unicity Network.com, Cure It Through the Grapevine: The Amazing Antioxidant Power of Grape Seed Extract, http://www.unicitynetwork.com/ibo/hwnews/health_wealth_110701.html.

\* cited by examiner

*Primary Examiner*—Amelia Owens
(74) *Attorney, Agent, or Firm*—Anton J. Hopen; Smith & Hopen, P.A.

(57) ABSTRACT

The present invention is an isolated compound and method of inducing endothelium-dependent relaxation in blood vessels including the step of introducing isolated procyanidins having a preponderance of (–)-epicatechins to a patient wherein the procyanidins are preferably galloylated. To achieve both bioavailability and potency, it is also preferred that the number of epicatechins monomers forming each procyanidin is between two and five. More specifically, isolated epicatechin-(4–8)-epicatechin-(4–8)-epicatechin-gallate (C1-gallate) is administered to the patient.

12 Claims, 10 Drawing Sheets

Fig. 6

Relaxation data and mass spectrometry information on Toyopearl fractions and HPLC peaks

| Toyopearl Fraction | HPLC Peak | EDR Threshold[a] (μg/ml) | ES-ITMS Peak Compounds |
|---|---|---|---|
| Fraction A | - | - | gallic acid; other phenolic acids |
| Fraction B | - | - | flavanol monomers (catechin, epicatechin) |
| Fraction C | - | > 4 | monomer-Gal. (ECG); dimers |
| Fraction D | D 1 | - | trimer |
|  | D 3 | > 4 | trimer |
|  | D 4 | - | trimer |
|  | D 6 | 2-3 | dimer-Gal. |
| Fraction E | E 1 | 1-2 | tetramer |
|  | E 2 | - | trimer |
|  | E 3 | 1 | trimer-Gal. |
|  | E 4 | 1 | tetramer |
| Fraction F | F 3 | 1-2 | tetramer |
|  | F 4 | 1 | dimer-Gal. |
|  | F 5 | 1-2 | tetramer |
|  | F 7 | 0.5-1 | trimer |
| Fraction G | G 2 | 1-2 | pentamer |
|  | G 3 | 2-4 | tetramer |
|  | G 4 | < 0.5 | tetramer-Gal. |
|  | G 5 | < 0.5 | tetramer-Gal. |
|  | G 6 | < 0.5 | trimer-Gal. |
|  | G 7 | < 0.5 | pentamer |

[a] Amount of fraction or peak material required to produce 15% relaxation.

Fig. 7

EC$_{50}$ values of the most active peaks.

| Peak # | Compound | EC$_{50}$ (C.I.)* |
|---|---|---|
| E1 | Tetramer | 2.59 (2.49 – 2.69) |
| E3 | Trimer-G | 1.55 (1.28 – 1.89) |
| E4 | Tetramer | 2.25 (2.14 – 2.37) |
| F3 | Tetramer | 1.54 (1.27 – 1.87) |
| F4 | Dimer-G | 1.25 (0.90 – 1.73) |
| F6 | Trimer | 1.17 (0.96 – 1.43) |
| G4 | Tetramer-G | 0.93 (0.83 – 1.04) |
| G5 | Tetramer-G | 0.57 (0.49 – 0.67) |
| G6 | Trimer-G | 1.00 (0.92 – 1.09) |
| G7 | Pentamer | 1.05 (0.85 – 1.29) |

* Mean concentration of peak material (μg catechin equivalents/ml) required to produce 50% relaxation (C.I. = 95% confidence interval).

VASODILATING COMPOUND AND METHOD OF USE

CROSS-REFERENCE TO RELATED APPLICATIONS

This application is a continuation-in-part of U.S. Provisional Application No. 60/332,428 filed Nov. 16, 2001. The disclosure of the provisional application is incorporated herein by reference.

FIELD OF INVENTION

This invention relates to compounds that demonstrate anti-oxidant and vascular properties, including vasodilation.

BACKGROUND OF THE INVENTION

The antioxidant properties of various plant favonoids, including procyanidins, are well known. Procyanidins possess endothelium-dependent relaxing (EDR) activity in blood vessels in vitro. The original finding that red wines, grape juice and other grape products exhibited EDR activity was companied by strong evidence that this activity was due to stimulation of nitric oxide (NO) production by the endothelial cells which form the lining of all blood vessels. Vasorelaxation induced by grape extracts, wines and the like was reversed by NO synthase inhibitors, and vasorelaxation could be restored by exposure of the vessel to L-arginine, the normal substrate for NO synthase. The importance of nitric oxide synthase system is underscored by the finding that a dysfunctional NO system can contribute to several diseases, including atherosclerosis. Therefore, consumption (and absorption) of NO-stimulating compounds in the diet, or in the form of dietary supplements, could contribute to prevention or halting the progress of atherosclerosis, other chronic age-related diseases, or conditions known to involve failure of the NO/NO synthase system, e.g., erectile dysfunction. Although procyanidin compounds, particularly those from grape seed extracts are known to exhibit EDR activity, current supplements administered to patients and consumers do not identify, nor isolate the active and most potent compounds to achieve the desired EDR.

SUMMARY OF INVENTION

The present invention is an isolated compound and method of inducing endothelium-dependent relaxation in blood vessels including the step of introducing isolated procyanidins having a preponderance of (−)-epicatechins to a patient wherein the procyanidins are preferably galloylated. To achieve both bioavailability and potency, it is also preferred that the number of epicatechins monomers forming each procyanidin is between two and five. More specifically, isolated epicatechin-(4–8)epicatechin-(4–8)-epicatechin-gallate (C1-gallate) is administered to the patient. To enhance endothelium-dependent relaxation, a concomitant administration of L-arginine may be performed.

BRIEF DESCRIPTION OF DRAWINGS

For a fuller understanding of the nature and objects of the invention, reference should be made to the following detailed description, taken in connection with the accompanying drawings, in which.

The original peak G6 at 0 time (A) was converted to the intermediate products (B) by acid thiolysis for 1 minute at 500 degrees centigrade. The only final products after 15 minutes at 50 degrees (C.) were epicatechin-gallate (ECG) and epicatechin-benzylthioether (Epi-BT). Thus it is concluded that peak G6 is epicatechin epicatechin-epicatechin-gallate (procyanidin trimer C1-gallate).

Figure 5:
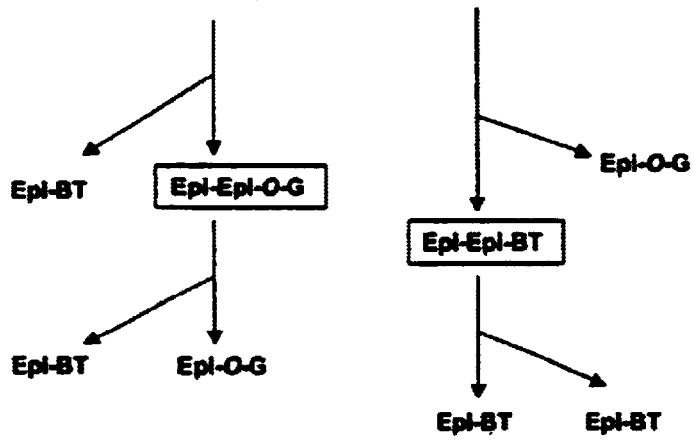

FIG. 5 is a diagrammatic view showing intermediate and final products of acid thiolysis of a procyanidin trimer gallate (C1-gallate) in the presence of benzyl mercaptan. "Lower" units (to the right in this illustration) are released by hydrolysis, whereas "upper" units (to the left) yield benzylthioethers (−BTs). The intermediate dimer products released after 1 minute at 50 degrees (epi-epi-O-G and epi-epi-BT) are subsequently broken down by thiolysis to yield the final products: epi-O-G and epi-BT.

FIG. 6 is a table of relaxation data and mass spectrometry information on Toyopearl fractions and HPLC peaks.

FIG. 7 is a table of $EC_{50}$ values of the most active peaks.

DETAILED DESCRIPTION

Grape Seed Extraction and Preliminary Fractionation

Concord grape seeds (provided by Welch Foods, Inc.) were crushed and extracted into methanol, concentrated, filtered, then applied to a column (35×2.5 cm, i.d.) filled with Toyopearl TSK HW-40 resin. Elution was carried out with methanol. Seven fractions were collected, evaporated, and redissolved in water (for EDR testing, HPLC analysis and tannase treatment) or methanol (for mass spectrometry and acid thiolysis).

Analytical HPLCA

Waters HPLC system was employed and consisted of a U6K injector, two 510 pumps, and a 481 UV/Vis detector, in conjunction with a Radial Pak reverse-phase NovaPak C18 column, protected by a guard column of the same material. The gradient for most analytical runs consisted of: Mobile phase A water; Mobile phase B—10% acetic acid in water, and the gradient ran from 25% B up to 75% B over the first 47 minutes; from 85 to 100% B over 47 to 50 minutes; and 100% B isocratic over 50 to 55 minutes. Thereafter the gradient was returned to mobile phase A to prepare for the next run. Flow rate was 0.7 mL/minute and detection was made at 280 nm. A different gradient was used for HPLC of acid thiolysis-treated samples: Mobile phase A 2.5% acetic acid; Mobile phase B 40% acetonitrile in A. The gradient ran from 10% B to 50% B in 20 minutes; up to 100% B at 25 minutes; isocratic at 100% B to 45 minutes; then back to 100% A for the next run.

Electrospray-ion Trap Mass Spectrometry (ES-ITMS)

Fractions eluted from the Toyopearl column and individual peaks were examined by mass spectrometry using a Bruker-Esquire ITMS with an electrospray ionization source and run in the negative ion mode. The electrospray matrix was 80% MeOH: 20% water. A syringe pump was used to deliver the samples to the needle with a flow rate of 25 µL/hr.

Chemical Analysis of Procyanidins

For determining whether or not EDR-active procyanidins were galloylated, purified samples in water were incubated with tannase (Sigma) at 35° for varying lengths of time, followed by HPLC analysis of the products. The acid thiolysis method was based on the method of Rigaud et al. (Micro method for the identification of proanthocyanidin using thiolysis monitored by high-performance liquid chromatography. J. Chrom. 540:40 1–405 (1991))which is incorporated herein by reference. The purified procyanidin sample in methanol was incubated with an equal amount of benzyl mercaptan solution (12% benzyl mercaptan in 0.4 HCl, made up in methanol) at 50° for varying lengths of time, followed by HPLC analysis of the products.

Aortic Ring Preparation and Bioassay of Fractions and Peaks

Male Sprague-Dawley rats (200–250 g) were euthanized with an overdose of sodium pentobarbital (100 mg/kg, i.p.), bled, and the thoracic aorta excised, cleaned, and rings (3–4 mm in length) were cut, taking care not to disturb the endothelium. In some instances the endothelium was deliberately removed by gently rubbing the lumen with a curved forceps. The rings were suspended in tissue baths containing a physiologic salt solution with the following composition (in millimolar): 118 NaCl; 4.7 KCl; 25 NaHCO3; 1.2 MgSO4; 1.2 NaH2PO4; 0.026 EDTA; 1.5 CaCl2; 11 glucose. The solution was bubbled continuously with $O_2/CO_2$ (95%/5%), and maintained at 37° C. Activity was recorded on a Grass polygraph. After equilibration for at least 1 hr under 1.5 g of tension, tissues were contracted submaximally (approximately 80% of Emax) with 1 µM phenylephrine, and then 3 µM acetyicholine, a known EDR-active compound, was added to the bath to test for intactness of the endothelium. This concentration of acetylcholine is sufficient to produce maximum endothelium-dependent relaxation in intact rings. Rings were washed with physiological salt solution three times over the next 45 minutes prior to the next sequence.

Screening of extracts, Toyopearl fractions, and HPLC peaks was conducted as follows. Aortic rings were contracted by addition of phenylephrine, and cumulative additions of each sample made, beginning with a concentration determined in preliminary experiments to be below the threshold for relaxation, and increased until a relaxation of approximately 15% (relative to the relaxation induced by 3 µM acetylcholine) was achieved. The concentration of sample required to produce this degree of relaxation (15%) was arbitrarily set as the "threshold" for demonstrating relaxation potency for the purpose of rapidly screening the many samples. Subsequently, full concentration-response curves were generated for peak compounds exhibiting the greatest relaxing activity. To test for endotheliumdependence, denuded aortic rings were used. Successful endothelium removal was established by a lack of relaxation response to 3 µM acetylcholine. Upon testing of the fractions and peaks, none exhibited any relaxing activity using de-endothelialized rings.

Toyopearl Fractionation

Figure 2:
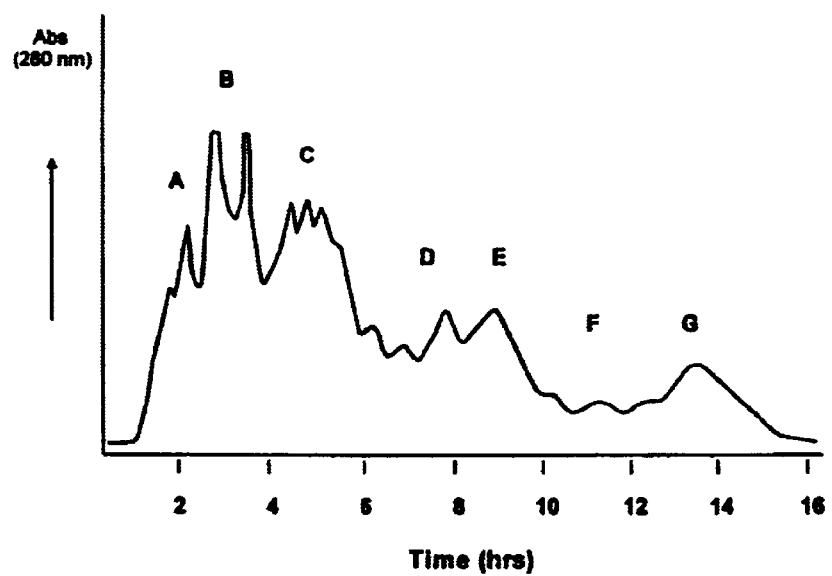
FIG. 2 is a Toyopearl TSK HW(40) elution profile of grape seed extract eluted with methanol, absorbance measured at 280 nm. Reprinted from Fitzpatrick et al.
Figure 3A:
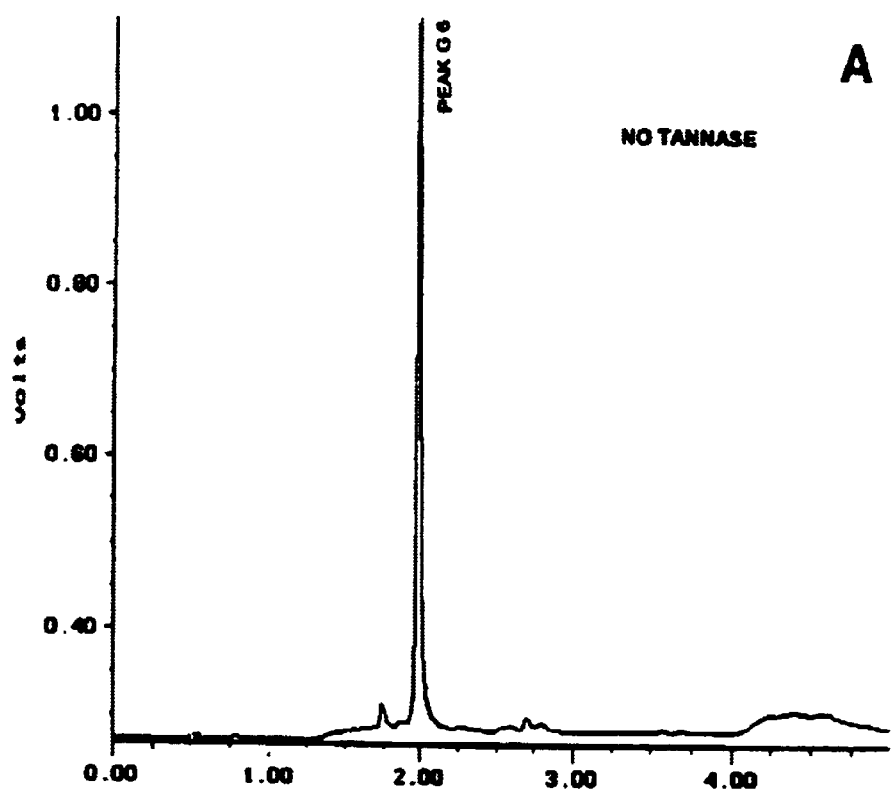
FIG. 3 shows the effect of tannase treatment on peak G6. The original peak G6 (A) was converted to gallic acid and apparently trimer C1 (B), based on retention time.
Figure 3B:
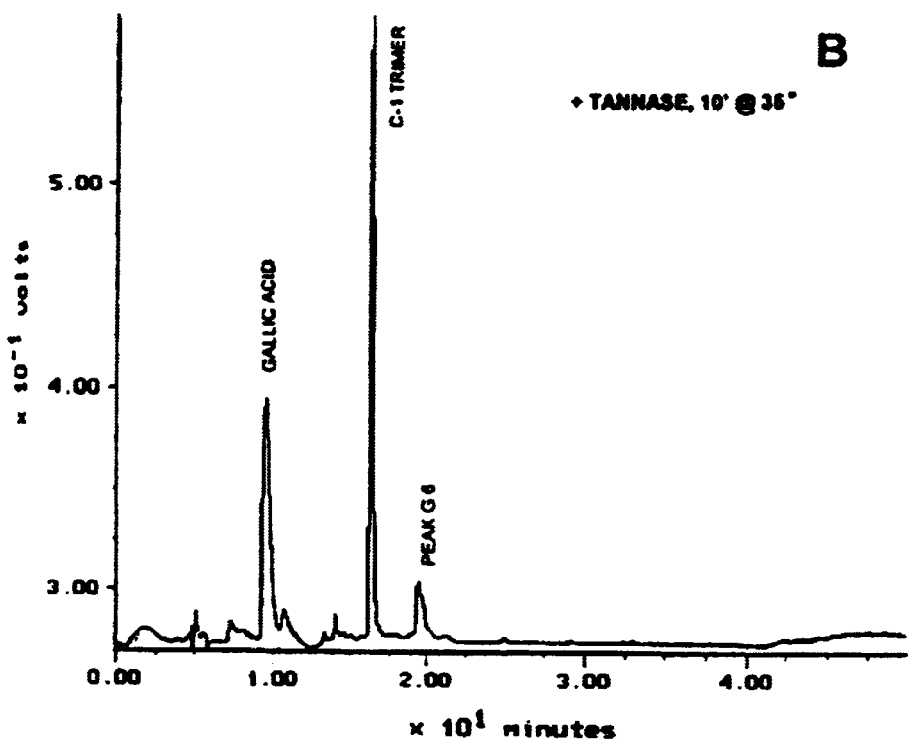

Toyopearl TSK HW-40S fractionation of grape seed polyphenolics using methanol as eluent yielded 7 fractions, labeled A through G (FIG. 2). The compounds present in the early fractions were easily identified by HPLC by their co-elution with available standards e.g., fraction A contained primarily gallic acid, fraction B contained (+)-catechin and (−)-epicatechin, and fraction C contained (−)-epicatechin gallate plus other compounds subsequently identified as flavan-3-ol dimers. These three fractions exhibited very little EDR activity when bioassayed, whereas the remaining Toyopearl fractions containing proanthocyanidins displayed varying degrees of vasorelaxing potencies.

EDR Activity of Toyopearl Fractions and HPLC Peaks

FIG. 6 summarizes the relaxation and ES-ITMS results for most of the Toyopearl fractions and for their constituent peaks. Some peaks were numbered initially, but were present in concentrations too small to collect and test for EDR activity, therefore are not listed in the table. Little or no relaxing activity was observed in fractions A, B, or C, which contained only phenolic acids, monomeric, and dimeric flavanol compounds, respectively, although fraction C (which also contains epicatechin-gallate) showed some relaxing activity at concentrations >4 µg/mL. Relatively more activity (indicated by the "threshold") was seen in subsequent fractions, with activity generally increasing from fraction D through fraction G. $EC_{50}$ values (with confidence intervals) of active Toyopearl fractions (fractions D G) were as follows: Fraction D=4.37 (1.30 14.60); Fraction E=2.97 (1.65 5.38); Fraction F=2.55 (1.75 3.72); and, Fraction G=1.20 (0.84 1.71). Fractions eluting later than fraction G (using 70% acetone in water) were quite active but were not pursued since they were higher molecular weight compounds that would not be bioavailable.

HPLC peaks derived from fractions E, F, and G that exhibited the greatest EDR activity are indicated in FIG. 7, along with their $EC_{50}$ values. These values ranged from approximately 0.6 µg/mL to 2.6 µg/mL. The most active compounds include proanthocyanidins larger than dimers (trimers, tetramers and pentamers), and their gallates. Galloylation appeared to increase activity at any given molecular size, e.g. the activity of trimer gallates was greater than that of most trimers, and dimer gallate activity was greater than that of the mostly inactive dimers. There also seem to be differences in EDR activity among the members of the isomeric families, e.g., all compounds identified as tetramers were not equally active, suggesting that the specific monomeric makeup of the compounds, and the order of the monomeric components within the oligomer, are important for activity.

Chemical Analysis of Peak G6

Peak G6 was selected for more detailed analysis because it is one of the smallest of the EDR-active compounds (and more bioavailable), and is more abundant in these seeds than are other smaller EDR-active procyanidins. This compound was determined to be a trimer gallate, according to ES-ITMS (FIG. 6 and 7). This was confirmed by treatment with tannase, which resulted in two HPLC peaks (FIG. 4A & 4B), gallic acid and another peak, tentatively identified as trimer C1 (epi-epi-epi).

Figure 1:
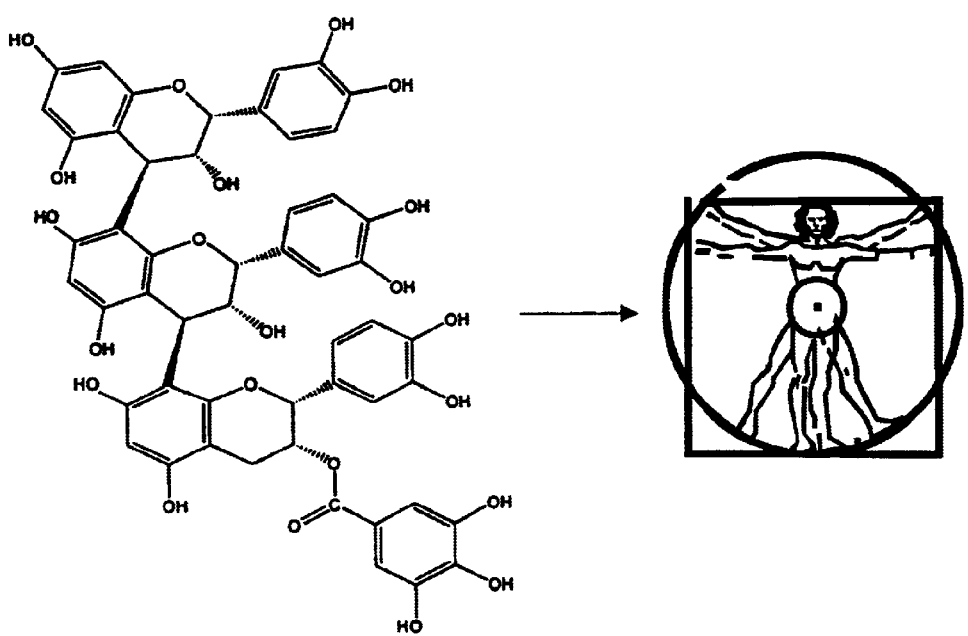
FIG. 1 is a diagrammatic view of the introduction of isolated epicatechin-(4–8)-epicatechin-(4–8)-epicatechin-gallate (C1-gallate) to a patient to induce endothelium-dependent relaxation.
Figure 4A:
FIG. 4 is the acid thiolysis of peak G6 in the presence of benzyl mercaptan B.M.
Figure 4B:
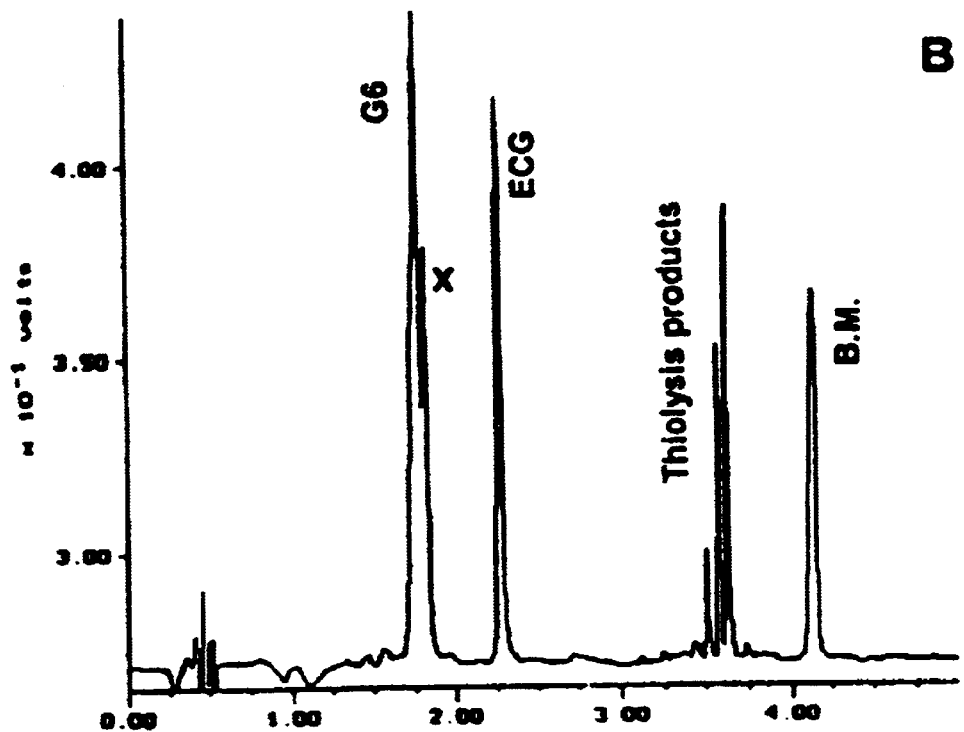
Figure 4C:
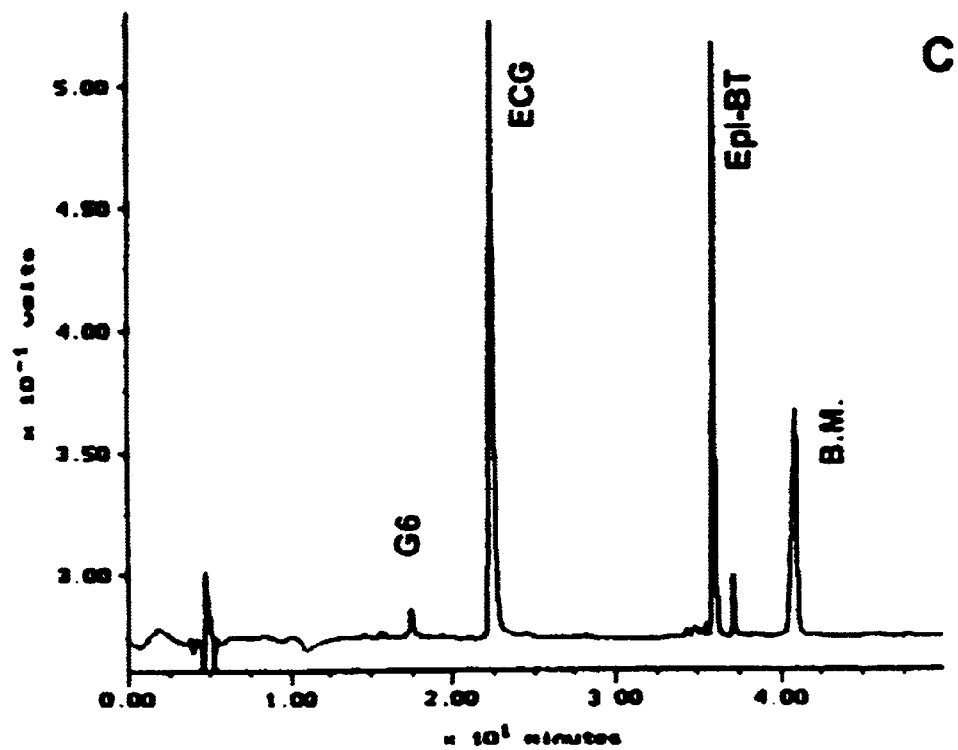

Partial acid thiolysis of peak 06 with benzyl mercaptan (1 minute incubation at 50°) yielded several intermediate products including epicatechin-gallate, an unidentified peak with a retention time of about 18 minutes (probably epicatechin-epicatechin-gallate, and 2 prominent peaks plus a small one at 35–36 mm (FIG. 4A & 4B). The latter were determined to be benzylthioethers (BT"s). Complete acid thiolysis (15"

at 50 degrees) yielded only 2 peaks, identified as epicatechin gallate and epicatechin-BT (FIG. 4C). These results indicate that Peak G6 is comprised only of epicatechins, with a gallate attached to one of the epicatechins. FIG. 5 shows the scheme for the breakdown products obtained, and that the compound is epicatechin-epicatechinepicatechin-gallate, with the gallate attached to the terminal epicatechin (gallate attachment on either of the other two epicatechins would yield entirely different breakdown patterns than the one described). The tannase results yielded a peak that appears to be C1 trimer (epi epi-epi), based on retention time. Therefore, the linkage is 4–8. The G6 compound structure, epicatechin-(4–8)-epicatechin-(4–8)epicatechin-gallate, is shown in FIG. 1.

These results are only one example that EDR activity is enhanced as the content of (−)-epicatechin in the oligomer increases, and that the presence of gallate(s) augments activity as well. The $EC_{50}$s of some of the more active of the compounds (FIG. 7) were in the low μg/ml and sub-μg/ml range.

These results empirically establish the utility of the claims of this novel invention. Individual compounds with biological activity can be purified and identified by the methods utilized here: solvent extraction, preliminary fractionation by Toyopearl chromatography, analysis by HPLC, ES-ITMS, tannase treatment, and acid thiolysis, with bioassay at each step, e.g. using the rat aortic ring preparation for determining EDR activity. The most active EDR-active compounds appear to be galloylated procyanidins containing a preponderance of (−)-epicatechins. Such compounds may be isolated from grape seeds on a large scale, or synthesized in bulk quantities.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described.

What is claimed is:

1. A method of inducing endothelium-dependent relaxation in blood vessels comprising the step of introducing isolated procyanidins having a preponderance of (−)-epicatechins to a patient.

2. The method of claim 1 wherein the procyanidins are galloylated.

3. The method of claim 1 wherein the number of epicatechins monomers forming each procyanidin is between two and five.

4. The method of claim 1 further comprising the step of concomitantly administering L-arginine to the patient.

5. A method of inducing endothelium-dependent relaxation in blood vessels comprising the step of introducing isolated epicatechin-(4–8)-epicatechin-(4–8)-epicatechin-gallate (C1-gallate) to a patient.

6. The method of claim 5 further comprising the step of concomitantly administering L-arginine to the patient.

7. A chemical compound for inducing endothelium-dependent relaxation in blood vessels comprising isolated procyanidins having a preponderance of (−)-epicatechins.

8. The chemical compound of claim 7 wherein the procyanidins are galloylated.

9. The chemical compound of claim 7 wherein the number of epicatechins monomers forming each procyanidin is between two and five.

10. The chemical compound of claim 7 further comprising L-arginine.

11. A chemical compound for inducing endothelium-dependent relaxation in blood vessels comprising isolated epicatechin-(4–8)-epicatechin-(4–8)-epicatechin-gallate (C1-gallate).

12. The chemical compound of claim 11 further comprising L-arginine.

* * * * *

UNITED STATES PATENT AND TRADEMARK OFFICE
CERTIFICATE OF CORRECTION

PATENT NO.    : 6,706,756 B1
DATED         : March 16, 2004
INVENTOR(S)   : David F. Fitzpatrick and Rebecca O'Malley It is certified that error appears in the above-identified patent and that said Letters Patent is hereby corrected as shown below:

<u>Title page,</u>
Item [75], Inventor, please add the following:
-- Rebecca O'Malley (U.S. Citizen)
  4202 East Fowler Avenue, SCA 400
  Tampa, Florida 33620 --

Signed and Sealed this

Twenty-fifth Day of May, 2004

JON W. DUDAS
*Acting Director of the United States Patent and Trademark Office*